United States Patent
Hack et al.

(10) Patent No.: US 9,220,414 B2
(45) Date of Patent: Dec. 29, 2015

(54) DENTAL CAMERA SYSTEM

(71) Applicant: Dürr Dental AG, Bietigheim-Bissingen (DE)

(72) Inventors: Alexander Hack, Biberach (DE); Peter Lais, Erlingheim (DE); Raimund Maier, Tamm (DE); Axel Schramm, Ilsfeld (DE)

(73) Assignee: Duerr Dental AG, Bietigheim-Bissingen (DE)

( * ) Notice: Subject to any disclaimer, the term of this patent is extended or adjusted under 35 U.S.C. 154(b) by 0 days.

(21) Appl. No.: 14/244,214

(22) Filed: Apr. 3, 2014

(65) Prior Publication Data

US 2014/0302452 A1 Oct. 9, 2014

(30) Foreign Application Priority Data

Apr. 4, 2013 (DE) .......................... 10 2013 005 616

(51) Int. Cl.
*H04N 5/225* (2006.01)
*A61B 1/04* (2006.01)
*A61B 5/00* (2006.01)
(Continued)

(52) U.S. Cl.
CPC ........... *A61B 5/0088* (2013.01); *A61B 1/00096* (2013.01); *A61B 1/00188* (2013.01); *A61B 1/00193* (2013.01); *A61B 1/24* (2013.01); *A61B 5/1079* (2013.01); *H04N 5/2254* (2013.01); *A61B 1/043* (2013.01); *H04N 2005/2255* (2013.01)

(58) Field of Classification Search
CPC ................................ A61B 6/145; A61B 1/055
USPC ................................................ 396/16; 348/66
See application file for complete search history.

(56) References Cited

U.S. PATENT DOCUMENTS 8,265,478 B1 9/2012 Georgiev
2009/0268208 A1 10/2009 Ertl
(Continued)

FOREIGN PATENT DOCUMENTS

DE 10 2008 017 481 A1 10/2009
DE 10 2009 017 819 A1 10/2010
(Continued)

OTHER PUBLICATIONS

Taheri, Arash et al.,"Focusing and depth of field in photography: application in dermatology practice," Skin Research and Technology, Jan. 7, 2013: 19; 394-397.
(Continued)

*Primary Examiner* — Clayton E Laballe
*Assistant Examiner* — Noam Reisner
(74) *Attorney, Agent, or Firm* — Factor Intellectual Property Law Group, Ltd.

(57) ABSTRACT

A dental camera system for creating an image of an object has a dental camera, which comprises a housing and optics arranged therein together with an image sensor. The dental camera system further comprises an evaluation unit which cooperates with the image sensor to capture the object. To achieve a dental camera system whereof the dental camera performs using optics without movable or controllable optical elements, it is provided for the optics to be plenoptic optics which are designed to determine a 4D light field when capturing the object and for the evaluation unit to be designed to calculate at least one representation of the captured object from the 4D light field.

10 Claims, 3 Drawing Sheets

(51) Int. Cl.
*A61B 1/00* (2006.01)
*A61B 1/24* (2006.01)
*A61B 5/107* (2006.01)

(56) References Cited

U.S. PATENT DOCUMENTS

2011/0080576 A1      4/2011   Thiel et al.
2012/0281072 A1*   11/2012   Georgiev et al. ............... 348/49
2013/0323673 A1*   12/2013   Hakomori et al. ............. 433/29
2014/0183334 A1*     7/2014   Wang et al. ................ 250/208.1

FOREIGN PATENT DOCUMENTS

| | | |
|---|---|---|
| DE | 10 2012 102 580 A1 | 9/2013 |
| JP | 2005069936 A1 | 3/2005 |
| WO | 2006/048163 A2 | 5/2006 |
| WO | 2009144729 A1 | 12/2009 |

OTHER PUBLICATIONS

Ng, Ren et al., "Light Field Photography with a Hand-held Plenoptic Camera," Stanford Tech Report, 2005.

* cited by examiner

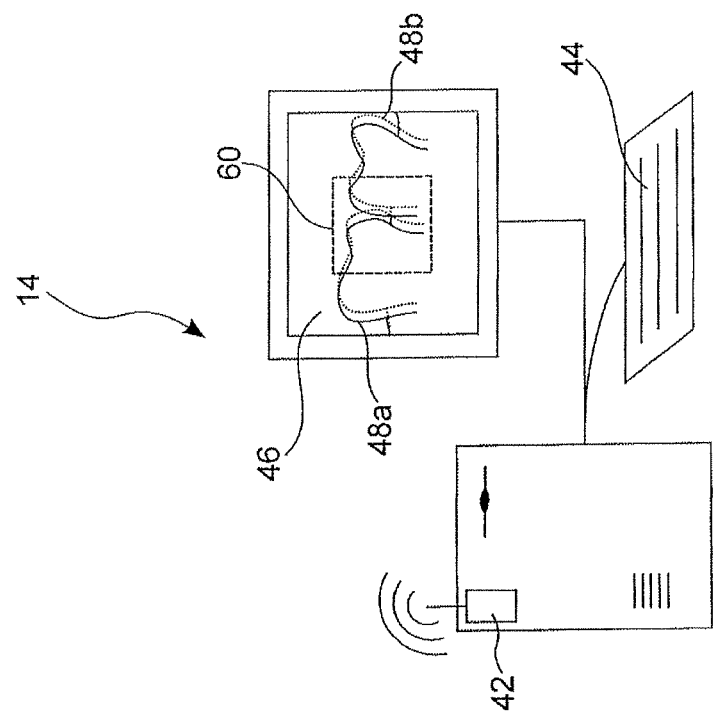
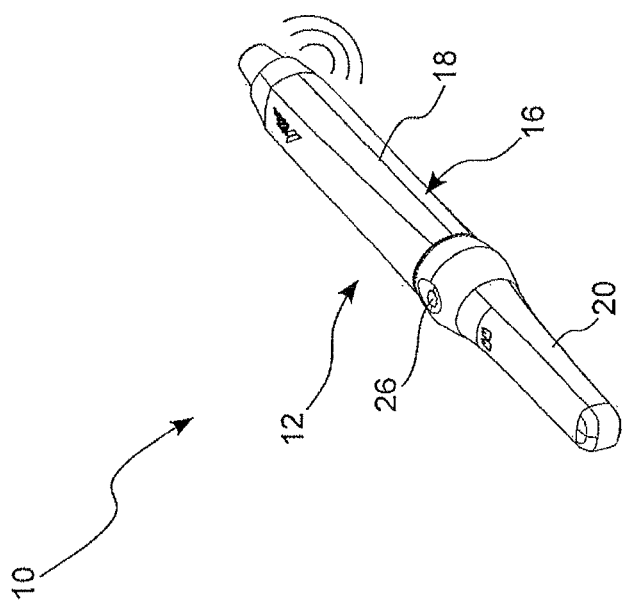
Fig. 1

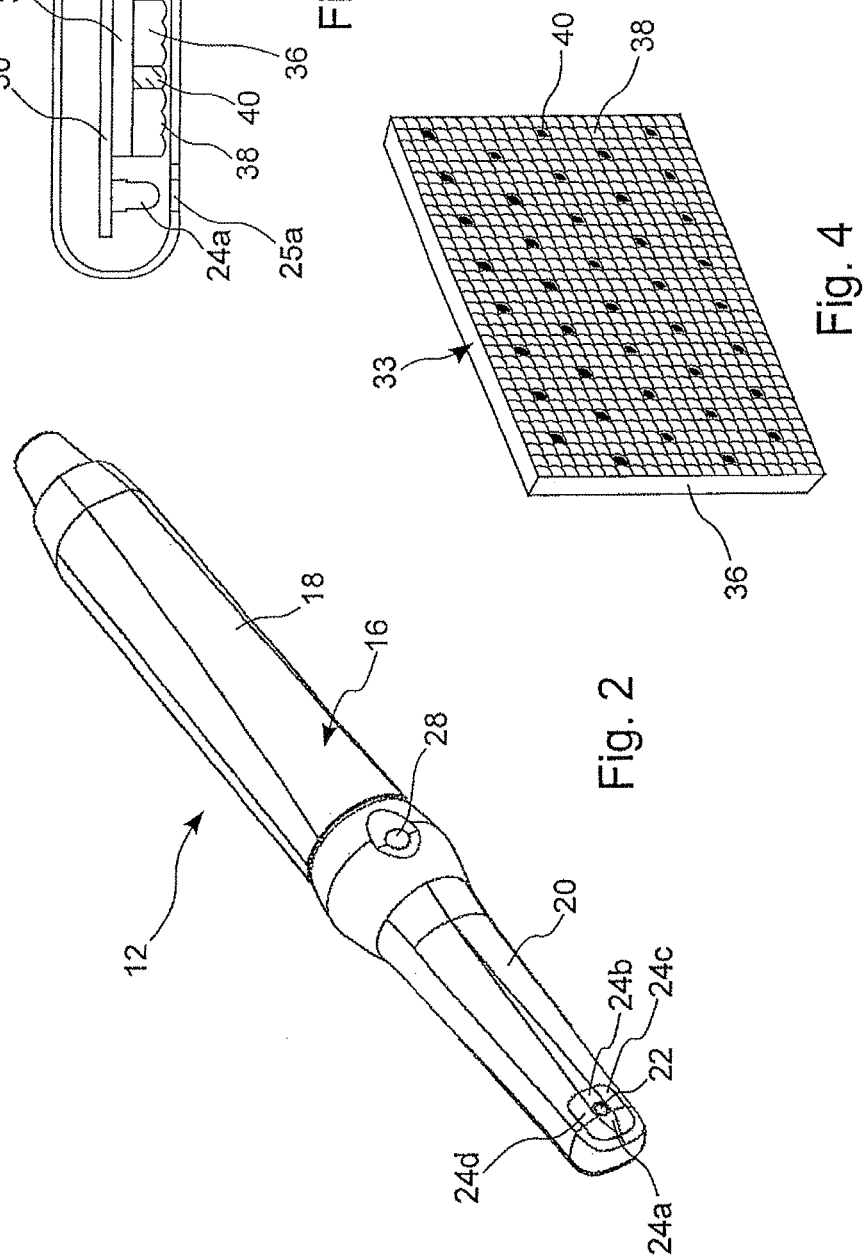

DENTAL CAMERA SYSTEM

CROSS-REFERENCE TO RELATED APPLICATIONS

The present application claims priority to German Patent Application No. 10 2013 005 616.0 filed Apr. 4, 2013, the contents of which are incorporated herein by reference.

FIELD OF THE INVENTION

The invention relates to a dental camera system for generating a representation of a tooth or another object.

BACKGROUND OF THE INVENTION

Dental camera systems are used in dentistry for taking photographs of the mouth, in particular the inside of the mouth and the teeth arranged therein. The representations produced by this can be displayed on a display device by the treating doctor for the purpose of diagnosis or for discussing treatment options with the patient. Moreover, the doctor can input the representations for long-term archiving in order to document the treatment process. A dental camera which is used in such systems is disclosed for example in DE 10 2009 017 819 A1.

Dental camera systems are furthermore known, which present further diagnostic options over a conventional imaging function. For example, dental camera systems are known in which caries bacteria or fluorescence markers linked thereto are excited into fluorescence with the aid of an excitation light which is mostly in the UV range. By measuring the fluorescent light subsequently emitted, it is possible to show the location of existing caries, which enables treatment to preserve the dental substance.

As revealed in the above-mentioned DE 10 2009 017 819 A1, dental cameras with a high image quality in particular usually have complex optics with a plurality of lenses. Moreover, dental cameras of this type must have individual movable components, such as a displaceable lens or a displaceable image sensor, to enable the object distance to be adjustable during the imaging process on the image sensor. Another option for adjusting the object distance consists in using liquid lenses in which the curvature of a boundary layer between two liquids is altered, thereby altering the refractive power of the liquid lens.

These known dental cameras are disadvantageous in that the optics are complex and large, which means that the camera head which is to be inserted inside the mouth cannot be less than a certain minimum size. Moreover, for precise displacement of the movable components, it is necessary to use mechanically complex drives which require control electronics. A similar situation applies to liquid lenses, for which control electronics are likewise required.

SUMMARY OF THE INVENTION

It is therefore an object of the invention to provide a dental camera system in which the optics of the dental camera do not require movable or controllable optical elements.

According to the invention, this may be achieved by a dental camera system with a dental camera which has a housing, optics arranged therein and an image sensor. The dental camera system further comprises an evaluation unit which cooperates with the image sensor to capture the object. According to the invention, the optics are plenoptic optics which are designed to determine a 4D light field when capturing the object. The evaluation unit is designed to render at least one representation of the captured object from the 4D light field.

The inventors have recognised that, for a dental camera, in particular for an intraoral camera, compactly designed optics with a high variability can be realised by plenoptic optics.

Conventional cameras reproduce the 3D area of the object on a 2D image, which is captured by the image sensor. A 2D image of this type does not contain any information relating to the direction from which a light beam captured by the image sensor has come. Conversely, in addition to the position and intensity of a light beam striking the image sensor, plenoptic cameras with plenoptic optics, which as such are known for example from publication U.S. Pat. No. 8,265,478 B1, also capture the direction thereof and therefore enable the 4D light field of an object to be captured. Since the 4D light field, also referred to as plenoptic function or brilliance, represents comprehensive information relating to the optical relationships of the captured object, it is possible with the aid of an evaluation algorithm stored in the evaluation unit to render a representation corresponding to a conventional 2D image from this 4D light field.

As will become clear below with respect to various further developments of the inventions, different image properties, such as the object distance, can be altered here retrospectively after the photograph is captured by way of the image sensor simply by changing different parameters of the evaluation algorithm or the evaluation algorithm itself without requiring movable or controllable optical elements in the dental camera for this purpose.

A plenoptic camera is notable in that the optics have an array of optical elements which split the beam path of the optics into a plurality of mutually adjacent imaging channels of which the fields of view partially overlap. Each optical channel therefore contains one or more optical elements. A partial overlapping of the fields of view is necessary so that, for each point of the object, information is present in a plurality of imaging channels to enable the 4D light field to be captured. An array, i.e. a grid arrangement, of optical elements enables the beam path of the optics to be split overall into a plurality of imaging channels of this type in simple manner. An aperture array, for example, or an array of Fresnel zone lenses or stepped lenses can be used for this.

However, it is preferably provided for the array of optical elements to be a lens array which comprises a plurality of lenses, with each lens being associated with one of the imaging channels.

A lens array, in particular a microlens array composed of a plurality of very small lenses (diameter ca. 10 µm-30 µm), is advantageous over an aperture array since it provides a better light yield. Since each of the lenses in the lens array captures the object at a slightly different viewing angle, an image of the object is produced on the image sensor within an image sensor region which is associated with an imaging channel at points which are slightly laterally offset from one another. The evaluation algorithm of the evaluation unit evaluates these offsets when rendering the representation of the object.

In an embodiment of the invention, the lenses of the lens array are the only lenses of the optics.

The optics of the dental camera therefore have a relatively simple construction. The preferably cumulative refractive power of the lenses of the lens array can be selected here so that the lens array can be arranged in the direct vicinity of the image sensor or in direct contact with this. It is therefore possible to produce a dental camera with a very compact camera head. The fact that no further lenses apart from the lenses of the lens array are provided along the beam path moreover renders the otherwise necessary precise mutual alignment of different lenses superfluous. However, it is still possible for other optical elements without a cumulative or dispersive effect, such as an entrance window or a filter, to be contained in the beam path of the optics.

In an embodiment of the invention, the imaging channels comprise a first group of imaging channels and a second group of imaging channels. A respective filter with a first filter effect is arranged in the beam path of the imaging channels of the first group and no filter, or a filter with a second filter effect which differs from the first filter effect, is arranged in the beam path of the imaging channels of the second group.

This enables the dental camera system to be used for example for fluorescence measurement purposes. Therefore, the first filter effect of the first group of imaging channels, which represents a proper subset of all imaging channels, can be selected for example so that only fluorescent light can pass through, which is emitted by the captured object through illumination by excitation light. The filter effect is selected here so that only wavelengths of greater than ca. 495 nm are captured in the respective imaging channel of the image sensor. In this arrangement, it is possible for example for only every tenth imaging channel to have a filter with a filter effect of this type. As a result of such optics, it is possible to capture conventional true-colour photographs on the one hand as well as fluorescent light measurements without a movable filter having to be inserted into, or removed from, the beam path. If the fluorescent light is sufficiently intense and the image sensor is appropriately sensitive, it is possible to capture a conventional image and a fluorescence image at the same time. The respective filters in the beam path can be arranged via a filter mask upstream or downstream of the array of optical elements in the beam path.

At least one filter with the first filter effect is preferably formed by a lens of the lens array here.

As a result, no further component has to be provided as a filter in the beam path. To produce a lens array of this type, it is possible to provide individual lenses with a filter effect which differs from the other lenses for example by coating, colourising or doping.

Alternatively or additionally to this, the image sensor itself can have a filter mask, which generates a wavelength-dependent sensitivity in selected regions of the image sensor.

In an embodiment of the invention, the plenoptic optics are constructed as focussed plenoptic optics.

This is advantageous in that it is possible to achieve a resolution which is adequate for dental photographs. In particular, the image distance from the lens array to the image sensor and the refractive power of the lenses are selected such that a plane of the object, which is at a normal operating distance for dental camera systems of ca. 5 mm to ca. 15 mm, preferably ca. 12 mm, is sharply imaged on the image sensor.

In an embodiment of the invention, the evaluation unit is designed to render representations of the object with different object distances from the 4D light field.

To this end, the evaluation unit uses a 4D light field evaluation algorithm, which is known as such and in which the object distance is taken into account as a parameter. By way of an input device, for example by way of a rocker switch on the dental camera, the user can specify the desired object distance here which, in a conventional dental camera system, corresponds to an alteration of the focal length. In a real-time evaluation of the 4D light field, it is possible to alter the parameters defining the object distance directly so that the representations are each rendered at the currently desired object distance. However, the evaluation algorithm can also firstly render a plurality of representations at different object distances and store these in the memory. The user can then select the representation with the desired object distance at a later time. With an appropriate design of the plenoptic optics, it is possible to freely select the desired object distance in a range between ca. 1 mm and ca. 300 mm, in particular between ca. 1 mm and ca. 55 mm, in particular between ca. 5 mm and ca. 45 mm, which is normal for dental cameras.

In an embodiment of the invention, the evaluation unit is designed to automatically select a representation from the representations at different object distances with the aid of a specifiable evaluation criterion.

With the aid of an evaluation criterion which evaluates the impression of sharpness of a representation, it is possible to automatically select that representation from the representations at different object distances which appears particularly sharp to the user. The selected representation is then shown on a display device. This enables a type of autofocus to still be realised in absolute terms after the object has been captured.

It can particularly be provided here for the at least one evaluation criterion to comprise a result of a contrast measurement in at least one sub-region of the representations.

The impression of sharpness of a representation can be evaluated by a contrast measurement, in particular an edge contrast measurement, in which image frequency components or edge thicknesses are determined. By way of an input device, it is possible here to define the sub-region of the representations (Region-of-Interest) in which the optimum impression of sharpness is to be determined.

In an embodiment of the invention, the evaluation unit is designed to render representations of the object with a different observer viewpoint from the 4D photographic image.

As a result of the different imaging channels arranged next to one another, it is possible within certain limits to freely select the observer viewpoint with an appropriate parameterisation of the evaluation algorithm. It is therefore possible to render and display representations of the object with a different observer viewpoint.

Provision is preferably made here for the evaluation unit to have a 3D display device, in particular an autostereoscopic screen, and to be designed to represent the captured object three-dimensionally using at least two of the images with a different observer viewpoint.

This enables an object, for example a tooth, to be represented spatially in that a representation as seen from a "left" observer viewpoint is selected for the left eye and a representation as seen from a "right" observer viewpoint is selected for the right eye. It is also possible here to select the distance between the two observer viewpoints by way of an input device, which enables a type of three-dimensional zoom onto the object or allows the properties of the 3D display to be adjusted.

The evaluation unit can furthermore be designed to measure the object three-dimensionally with the aid of the 4D light field.

As a result of the comprehensive information contained in the captured 4D light field, it is possible to measure the captured object three-dimensionally with the aid of a depth evaluation algorithm in the evaluation unit. This means that it is possible to generate a three-dimensional model, for example of a biting surface of a tooth, which optionally replaces a classic mechanical impression of the biting surface. In this regard, this embodiment of the invention represents a notable innovation since previous systems for the three-dimensional measurement of teeth were always realised in separate diagnostic devices with the aid of laser scanners. In the present invention, the three-dimensional measurement can preferably be supported by illuminating the object to be captured with the aid of a light source with a predetermined light pattern. To this end, it is for example possible to use an LED with a mask which generates a stripe or dot pattern on the illuminated object. Moreover, individual lenses of the lens array or groups of lenses can have a refractive power which deviates from the other lenses in order to provide the depth evaluation algorithm with additional depth information relating to the object.

A lens array of this type, which has lenses with a different refractive power, can also be advantageous in terms of rendering the representations of the object at different object distances. This is because this increases the range of the object distances in which it is possible to render representations which are sufficiently sharp. A relatively large range of ca. 1 mm to ca. 300 mm object distance is preferably covered so that the dental camera without moveable parts can be used both for macro photographs of individual teeth and for facial photographs of the patient.

It is to be understood that the aspects and objects of the present invention described above may be combinable and that other advantages and aspects of the present invention will become apparent upon reading the following description of the drawings and detailed description of the invention.

BRIEF DESCRIPTION OF THE DRAWINGS

The invention is explained below with the aid of exemplary embodiments with reference to the drawings, which show:

FIG. 1 a schematic illustration of the dental camera system according to the invention with a dental camera and an evaluation unit;

FIG. 2 a perspective view of the dental camera from below;

FIG. 3 a longitudinal section through a head portion of the dental camera;

FIG. 4 a perspective view of a microlens array, which is arranged upstream of an image sensor of the dental camera;

DETAILED DESCRIPTION OF THE PRESENT INVENTION

Figure 5:
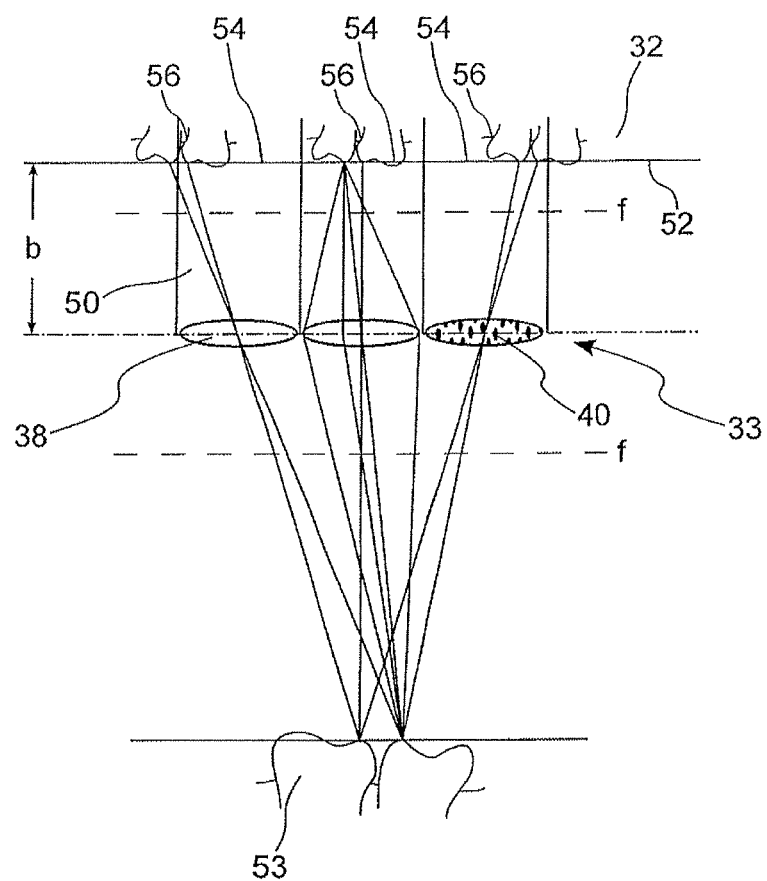
FIG. 5 a schematic illustration of the plenoptic optics used in the dental camera according to the invention.

FIG. 1 shows a dental camera system, denoted as a whole by 10, with a dental camera 12 and an evaluation unit 14.

The dental camera 12 has a housing 16 which extends substantially along a longitudinal axis and comprises a grip portion 18 on which the investigating doctor guides the dental camera 12. Arranged at the distal end of the housing 16 as seen by the doctor, there is a head portion 20 which is slimmer than the grip portion 18 and is guided into the oral cavity of a patient.

As can be seen in FIG. 2, arranged at the end of the head portion 20, there is an entrance window 22 which can be aligned in the direction of an object to be captured, for example a tooth, by positioning and rotating the dental camera 12. Various illuminating devices 24a to 24d, which are described in detail below, are arranged around the entrance window 22.

To activate different functions, the grip portion 18 furthermore has a still image switch 26 and a mode selection switch 28 as actuating switches which are diametrically opposed with respect to the longitudinal axis of the dental camera 12.

As shown in FIG. 3, a printed circuit board 30 which extends along the longitudinal axis, is arranged in the interior of the housing 16. Arranged on this printed circuit board 30 in the region downstream of the entrance window 22, there is an image sensor 32 which is electrically connected via the printed circuit board 30 to a control and communication module 34 by way of which the dental camera 12 is in communication with the evaluation unit 14, for example by WLAN.

The illuminating devices 24a to 24d, of which the two illuminating devices 24a and 24b in the form of LEDs are each shown behind exit windows 25a and 25b in the longitudinal section, are arranged around the image sensor 32, likewise directly on the printed circuit board 30. The illuminating devices 24a to 24d are also electrically connected to the control and communication module 34, which can switch the illuminating devices 24a to 24d on and off independently of one another.

The electrical systems of the dental camera 12 are supplied with energy by way of an energy store (not shown) in the grip portion 18.

As can further be seen from FIG. 3, the image sensor 32 supports a lens array 36 as plenoptic optics 33, which has a plurality of lenses 38 arranged next to one another in grid form. The plenoptic optics 33 further comprise apertures (not shown) with a fixed aperture opening which are associated with the individual lenses 38 of the lens array 36. To this end, an aperture mask made of non-transparent material can be encapsulated in the lens array 36, which is made from a substantially transparent material, in the manner of a compact layer system.

As can be seen from the perspective illustration in FIG. 4, individual lenses 38, here denoted as filter lenses 40, have a filter effect which deviates from the other lenses 38, as shown schematically by a corresponding colourisation of the filter lenses 40. This filter effect can be achieved by coating, colourising or dosing the individual filter lenses 40 or it can be realised in accordance with the aperture mask by way of a filter mask which is encapsulated in the lens array 36.

As shown in FIG. 1, the evaluation unit 14, which is constructed here as a commercially available PC, is in communication with the control and communication module 34 of the dental camera 12 via a communication module 42 so that the image data captured by the image sensor 32 is optionally transmitted to the evaluation unit 14 with the aid of a suitable compression procedure.

The evaluation unit 14 shown here further comprises a keypad 44 as an input device, although it is also possible to provide input devices which are specifically optimised for use in a dental camera system 10 and for which the user has only a few absolutely necessary input controls. The evaluation unit 14 receives additional input signals from the still image switch 26 and the mode selection switch 28 of the dental camera 12, for which the switch status, like the image data, is transmitted via the communication connection.

Finally, the evaluation unit 14 has an autostereoscopic screen 46 as a 3D display device. Autostereoscopic screens 46 are known in the prior art and can display different representations 48a, 48b for example using a cylindrical lens mask for the different viewing directions of the left and the right eye.

The dental camera system 10 operates as follows:

As can be seen in FIG. 5, the beam path of the optics 33 is split into a plurality of adjacently arranged imaging channels 50 as a result of the preceding lens array 36, which imaging channels each comprise separate conventional optics. A capture surface 52 of the image sensor 32 is split accordingly into a plurality of image sensor regions 54.

The image distance b between the capture surface 52 and the lens array 36 and the focal length f of the lenses 36 are selected here such that a plane of an object 53 which is located at a normal operating distance for dental cameras (12 mm here by way of example) is sharply imaged onto the capture surface 50. Whilst a photograph is taken by the dental camera 12, different images 56 of the object 53 are then captured at the same time in the image sensor regions 54 for the different imaging channels 50, with the respective observer positions and viewing directions differing slightly from imaging channel 50 to imaging channel 50 according to the position of the imaging channel 50.

With the aid of the control and communication module 34, the individual images 56 captured by the image sensor 32 are transmitted to the evaluation unit 14. In this, a plenoptic evaluation algorithm is processed, which determines the 4D light field with the aid of the different images 56.

From this 4D light field, the evaluation unit 14 generates two complete representations 48a, 48b of the object 53, each with a different observer viewpoint for the left and right eye, and displays these on the autostereoscopic screen 46.

The evaluation unit 14 can furthermore render representations 48a, 48b with different object distances from the 4D light field and select one or, in the case of the 3D display, two sharp representations 48a, 48b from these representations. To this end, an edge contrast measuring process, which evaluates the contrast and the thickness of edges in the representations 48a, 48b by way of frequency analysis, is applied for example in a central sub-region 60 of the representations 48a, 48b as an evaluation criterion for selection purposes. The evaluation unit 14 then provides an autofocus function which takes place after the actual photograph is taken by way of an optimising process, which varies the calculated object distance of the representations 48a, 48b and uses the result of the edge contrast measuring process as a variable to be optimised.

The representations 48a, 48b are updated in real time so that the respective object 53 which has just been captured by the dental camera 12 is displayed on the screen 46. By activating the still image switch 26, the user can trigger a still image function so that the currently displayed representations 48a, 48b are displayed until further notice and optionally archived.

The mode selection switch 28 can be used to convert the dental camera system 10 into 3D measuring mode. In this operating mode, a depth evaluation algorithm is activated, with the aid of which depth information, such as the bite profile of a photographed tooth, is obtained from the 4D light field, displayed and/or stored. The illuminating device 24b, which generates a stripe pattern on the object 53 with the aid of a stripe mask 62, is activated to support the depth evaluation algorithm.

A further operating mode which can be activated by way of the mode selection switch 28 is a fluorescence detection mode in which the illuminating device 24a, here in the form of a UV LED, is activated to generate excitation light. The excitation light generated in this way serves to excite fluorescence in caries bacteria, so that fluorescent light is emitted which strikes the lens array 36 through the entrance window 22. Here, all light components apart from the fluorescent light are substantially filtered out of the beam path at the filter lenses 40, so that only the fluorescent light is captured in the associated imaging channels 50. A fluorescence evaluation algorithm then only takes account of the images 56 pertaining to the filter lenses 40. It is thus possible to show the location of caries. With the aid of a pulse mode of the illumination devices 24a to 24d and a corresponding evaluation of the images 56 pertaining to the other lenses 38, true-colour representations 48a, 48b of the object 53, in which the caries detected by way of the fluorescence measurement are shown for example by false colours, are rendered and displayed at virtually the same time.

In a modification of the illustrated lens array 36 with a rectangular rid arrangement of the lenses 38, it is also possible to arrange these for example in a hexagonal pattern.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

The invention claimed is:

1. A dental camera system comprising:
   a) a dental camera comprising an image sensor and plenoptic optics arranged in a light path between an object and the image sensor,
   b) an evaluation unit that
      cooperates with the image sensor and
      is configured
         to calculate a 4D light field from data produced by the image sensor in a single image capture,
         to calculate different 2D image representations of the object from the 4D light field, which different 2D image representations correspond to 2D images captured at different object distances and
         to automatically select a 2D image representation from the different 2D image representations with the aid of at least one predetermined evaluation criterion, wherein the at least one evaluation criterion comprises a result of a contrast measurement in at least one sub-region of the different 2D image representations.

2. The dental camera system according to claim 1, wherein the plenoptic optics comprise an array of optical elements which splits the light path into a plurality of mutually adjacent imaging channels having partially overlapping fields of view.

3. The dental camera system according to claim 2, wherein the array of optical elements is a lens array which comprises a plurality of lenses, with each lens being associated with one of the imaging channels.

4. The dental camera system according to claim 3, wherein the lenses of the lens array are the only lenses of the dental camera.

5. The dental camera system according to claim 2, wherein the imaging channels comprise a first group of imaging channels and a second group of imaging channels, and wherein a filter with a first filter effect is arranged in the light path of the respective imaging channels of the first group and no filter, or a filter with a second filter effect which differs from the first filter effect, is arranged in the light path of the respective imaging channels of the second group.

6. The dental camera system according to claim 5, wherein the array of optical elements is a lens array which comprises a plurality of lenses, with each lens being associated with one of the imaging channels and wherein at least one filter with the first filter effect is formed by a lens of the lens array.

7. The dental camera system according to one of the preceding claims, wherein the plenoptic optics are designed as focussed plenoptic optics.

8. The dental camera system according to claim 1, wherein the evaluation unit is configured to calculate different 2D image representations of the object from the 4D light field, which different 2D image representations correspond to 2D images captured from a different observer viewpoint.

9. The dental camera system according to claim 8, wherein the evaluation unit comprises a 3D display device, in particular an autostereoscopic screen, and is configured to display the captured object three-dimensionally using at least two of the different 2D image representations.

10. The dental camera system according claim 1, wherein the evaluation unit is configured to calculate a three-dimensional structure of the object from the 4D light field.

* * * * *